(12) United States Patent
Shuen

(10) Patent No.: US 6,237,788 B1
(45) Date of Patent: May 29, 2001

(54) PERFUME BOTTLE STRUCTURE

(75) Inventor: Shun Tian Shuen, San Chung (TW)

(73) Assignee: Janchy Enterprise Co., Ltd., San Chung (TW)

(*) Notice: Subject to any disclaimer, the term of this patent is extended or adjusted under 35 U.S.C. 154(b) by 0 days.

(21) Appl. No.: 09/577,573

(22) Filed: May 25, 2000

(51) Int. Cl.⁷ .............................. B65D 23/02; B65D 90/12
(52) U.S. Cl. .................. 215/12.1; 215/376; 215/386; 220/253; 220/4.23; 220/4.24; 220/630; 206/823; 206/457
(58) Field of Search .................................. 245/237, 386, 245/311, 376, 313, 12.1; 220/835, 253, 4.21, 4.22, 4.24, 4.25, 630; 206/823, 581, 457, 386

(56) References Cited

U.S. PATENT DOCUMENTS

| | | | |
|---|---|---|---|
| 1,741,154 | * 12/1929 | Haigney | 215/12.1 |
| 2,093,905 | * 9/1937 | Bowen | 215/12.1 |
| 2,328,338 | * 8/1943 | Hauptman | 215/12.1 |
| 3,945,568 | * 3/1976 | Bychowski | 220/4.25 X |
| 5,125,521 | * 6/1992 | Somogyi | 215/12.1 |

* cited by examiner

Primary Examiner—Allan N. Shoap
Assistant Examiner—Tri M. Mai
(74) Attorney, Agent, or Firm—Bacon & Thomas, PLLC

(57) ABSTRACT

Perfume bottle structure including an upper casing and a lower casing mated with each other. The upper and lower casings are respectively housed in two frame bodies and the surfaces of the upper and lower casings are disposed with replaceable decorative articles. A perfume container is placed in the lower casing and connected with a base seat for firmly locating the perfume container. A fixing seat is mounted at bottom end of the lower casing for freely firmly locating the perfume bottle at desired places. The top end of the upper casing is formed with a cylindrical cavity in which a cylindrical sleeve is fitted. A decorative cap is engaged with the cylindrical sleeve for opening/closing the perfume bottle.

1 Claim, 5 Drawing Sheets

PERFUME BOTTLE STRUCTURE

BACKGROUND OF THE INVENTION

The present invention relates to a novel perfume bottle structure which achieves a decorative effect and can be firmly freely placed at desired places.

A conventional perfume bottle has monotonous pattern without any decorative effect. Moreover, after a period of use and the perfume contained in the perfume bottle is exhausted, it is impossible to open the perfume bottle for replacing the perfume. Under such circumstance, the entire perfume bottle will lose its function and must be discarded. This leads to waste of resource.

SUMMARY OF THE INVENTION

It is therefore a primary object of the present invention to provide a novel perfume bottle structure including easily detachable decorative articles and frame bodies, whereby the assembly of the perfume bottle can be changed to enhance the appearance.

It is a further object of the present invention to provide the above perfume bottle structure which has simple structure and can be easily mass-produced.

It is still a further object of the present invention to provide the above perfume bottle structure which is equipped with a fixing seat having double-face gum so that the perfume bottle can be freely firmly located at a desired place to achieve a decorative effect.

The present invention can be best understood through the following description and accompanying drawings wherein:

DETAILED DESCRIPTION OF THE PREFERRED EMBODIMENT

Figure 1:
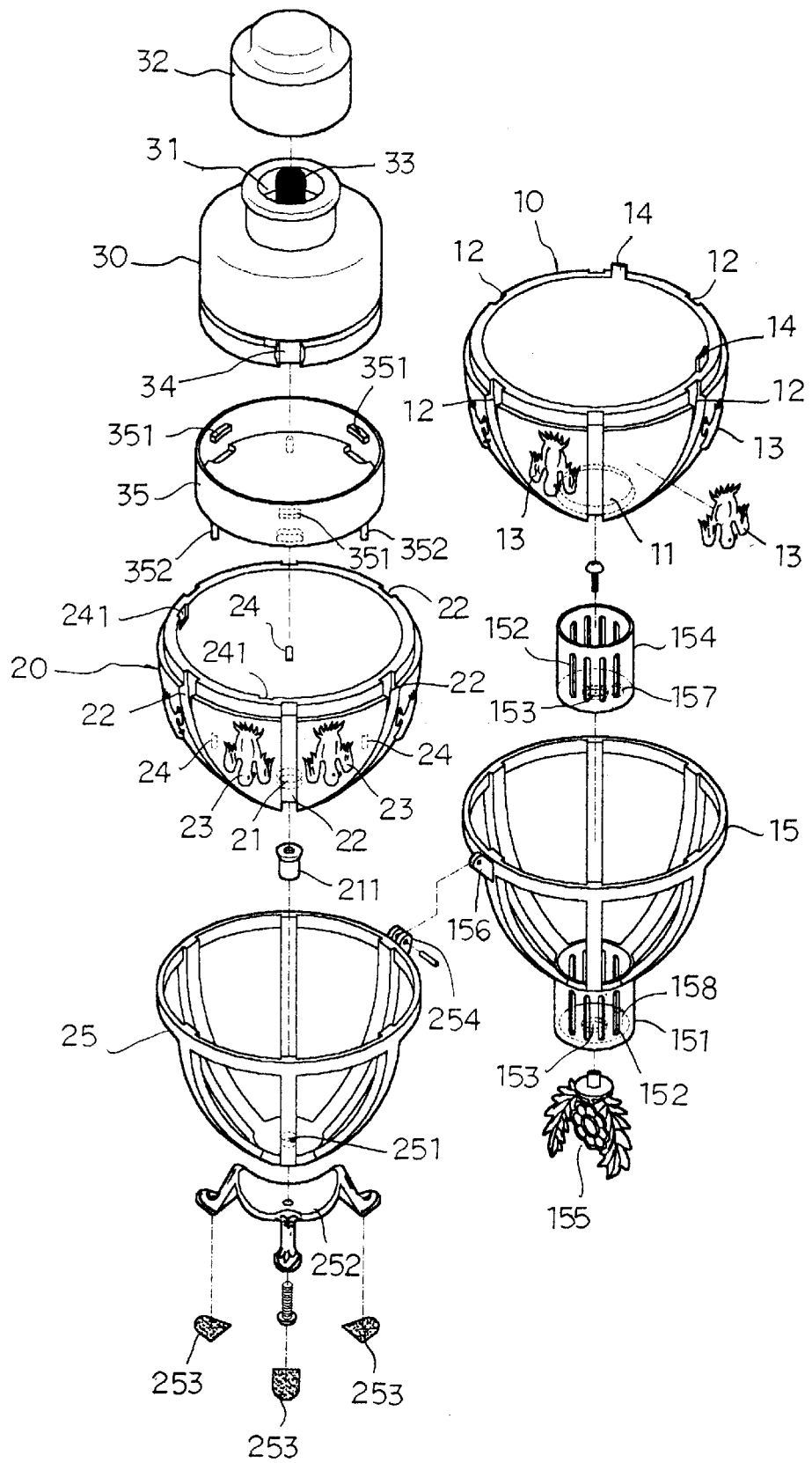
FIG. 1 is a perspective exploded view of the present invention.
Figure 2:
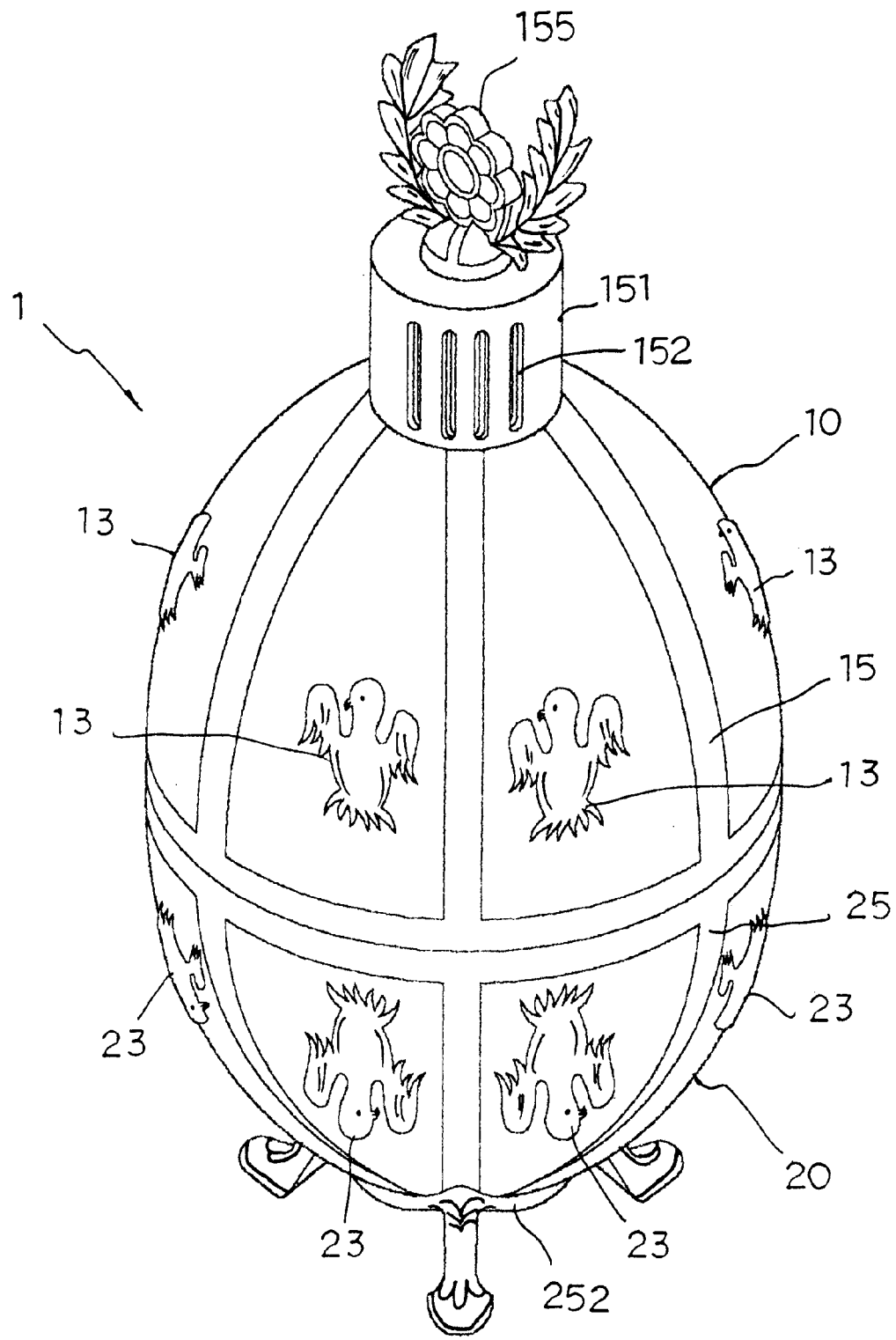
FIG. 2 is a perspective assembled view of the present invention.

Please refer to FIGS. 1 and 2. The perfume bottle structure 1 of the present invention includes an upper casing 10, a lower casing 20 and a perfume container 30.

As shown in FIG. 1, the upper casing 10 is a semi-elliptic casing the top end of which is formed with a perforation 11. The upper casing 10 is further formed with several grooves 12 at equal intervals. The grooves 12 downward extend from the perforation 11 to the edge of an open end. A decorative article 13 is replaceably disposed on a surface defined between each two adjacent grooves 12. The edge of inner wall face of the upper casing 10 is formed with projecting locating plates 14. The lower casing 20 is formed with corresponding recesses 241, whereby when the upper and lower casings 10, 20 are mated with each other, the locating plates 14 are inserted into the recesses 241. The upper casing 10 is housed in a frame body 15 having similar profile and slightly larger dimension. The top end of the frame body 15 is formed with a cylindrical cavity 151. The periphery of the cavity 151 is formed with several slits 152 and a central through hole 153. A locating post 158 is disposed on one side of the through hole 153. A cylindrical sleeve 154 having same structure but slightly smaller dimension is received in the cavity 151. The sleeve 154 is formed with a central through hole 153 and an arch slide slot 157 beside the central through hole 153 corresponding to the locating post 158 for the locating post 158 to slidably insert therein. A decorative cap 155 with free pattern is fitted in the central through hole 153 of the cylindrical cavity 151. A screw is passed through the sleeve 154 to lock the decorative cap 155 with the sleeve 154. In addition, a lug 156 is disposed on the edge of the opening of the frame body 15.

The lower casing 20 has a semi-elliptic structure basically identical to that of the upper casing 10. The bottom end of the lower casing 20 is formed with a perforation 21. The periphery of the lower casing 20 is further formed with several grooves 22 at equal intervals. The grooves 22 upward extend from the perforation 21 to the edge of an open end. A decorative article 23 is replaceably disposed on a surface defined between each two adjacent grooves 22. The perfume container 30 is placed into the internal chamber of the lower casing 20. The inner wall face of the lower casing is annularly formed with several dents 24 at equal intervals. The edge of the inner wall face is formed with recesses 241. The lower casing 20 is housed in a frame body 25 with similar profile but slightly larger dimension. The bottom end of the frame body 25 is formed with a through hole 251. A tripod-like fixing seat 252 is disposed around the outer face of the through hole 251. Each leg of the fixing seat is disposed with double-face gum 253 for reliable standing. A screw is passed through the fixing seat 252 and the through hole 251 to lock the fixing seat 252 with a stop block 211 so as to associate the fixing seat 252, the frame body 25 and the lower casing 20 into an integral body. In addition, a connecting arm 254 is disposed on the edge of the opening of the frame body 25 corresponding to the lug 156.

The perfume container 30 contains a perfume therein. One end of the perfume container 30 is formed with a narrowed neck section having an opening 31 sealed by a cover body 32. A wick 33 is positioned in the container 30 for absorbing the perfume and releasing the perfume into the air,. The periphery of the bottom face of the perfume container 30 is formed with notches 34 at equal intervals and is equipped with a base seat 35. The inner wall face of the base seat 35 is formed with ribs 351 at equal intervals corresponding to the notches 34, whereby the perfume container 30 can be fitted into the base seat 35 and rotated so as to engage with the base seat 35. In addition, the bottom of the base seat 35 is disposed with several locating projections 352 for inserting into the dents 24 of the inner wall face of the lower casing 20 so as to associate the base seat 35 with the lower casing 20.

Figure 3:
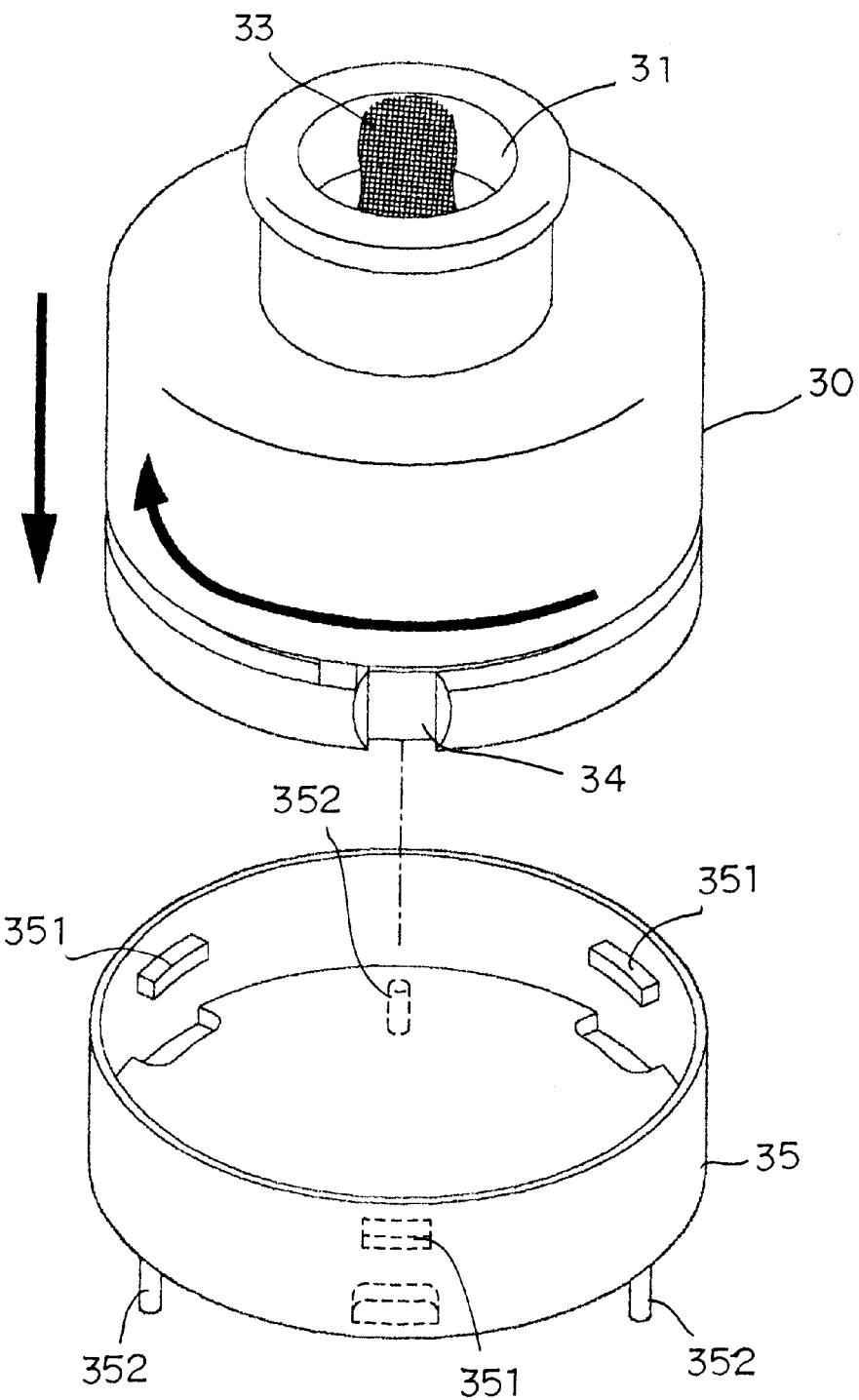
FIG. 3 is a perspective view showing the connection between the perfume container and the base seat of the present invention.

According to the above arrangement, when assembled, the upper and lower casings 10, 20 are respectively assembled with the frame bodies 15, 25 which are snugly fitted into the grooves 12, 22 of outer surfaces of the upper and lower casings 10, 20. Then the lug 156 and connecting arm 254 of the two frame bodies 15, 25 are connected with each other by means of an insertion pin, whereby the two frame bodies 15, 25 can be opened or closed. Then the base seat 35 is placed into the lower casing 20 with the locating projections 352 inserted into the dents 24. At this time, the perfume container 30 is placed in with the ribs 351 of the base seat 35 passing through the notches 34 of the perfume container 30. Then the perfume container 30 is rotated to firmly associate with the base seat 35 as shown in FIG. 3 to form a complete perfume bottle structure as shown in FIG. 2.

Figure 4:
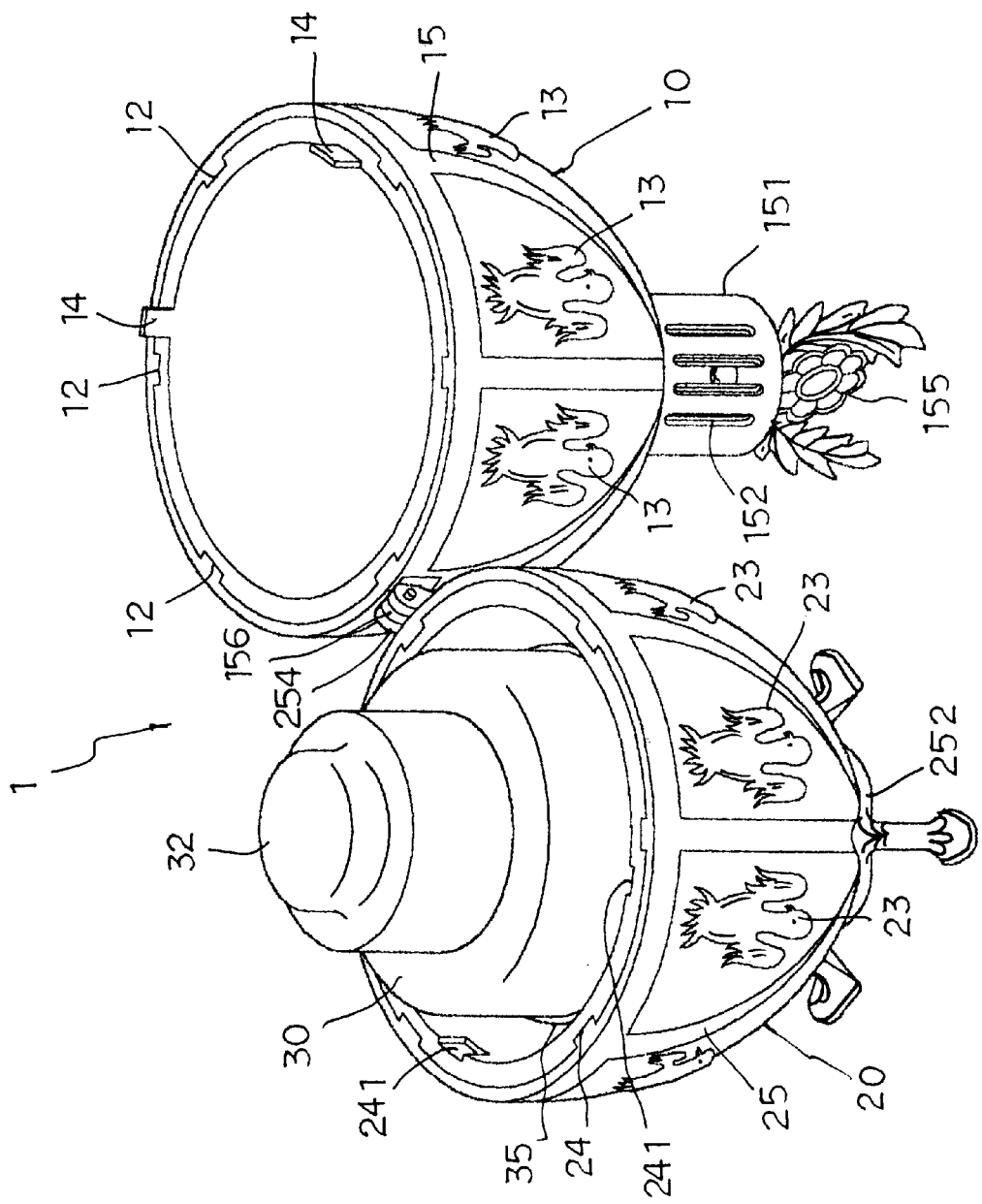
FIG. 4 is a perspective view showing the upper and lower casings of the present invention in an opened state.
Figure 5:
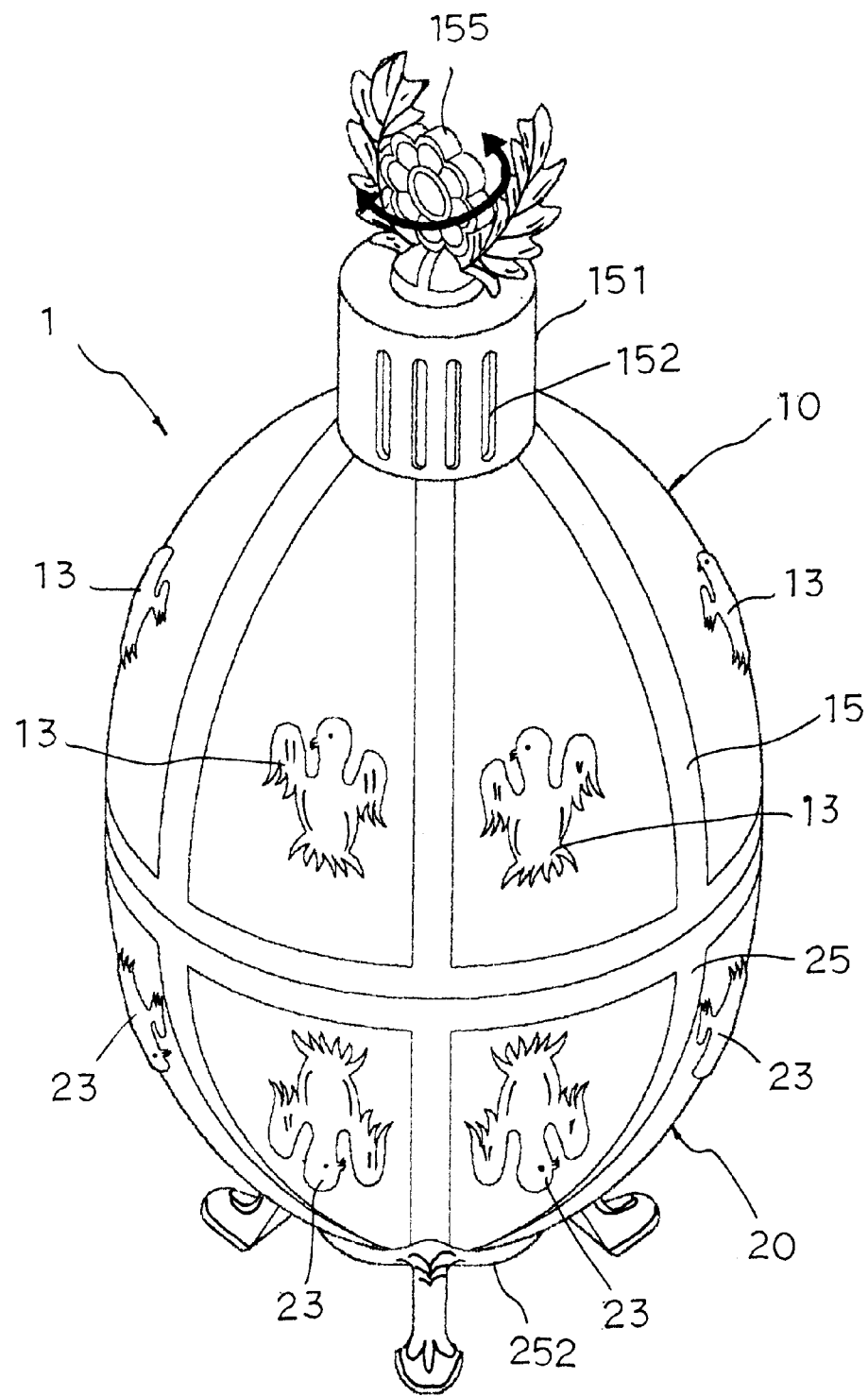
FIG. 5 is a perspective view showing the use of the present invention.

Prior to use, as shown in FIGS. 4 and 5, the two frame bodies 15, 25 together with the upper and lower casings 10, 20 are opened to form a state as shown in FIG. 4. Then the cover body 32 of the perfume container 30 is screwed open and then the upper casing 10 and the frame body 15 are closed to form a state as shown in FIG. 5. In use, the decorative cap 155 is manually rotated to drivingly rotate the cylindrical sleeve 154. At this time, the slits 152 of the periphery of the sleeve 154 are communicated with the slits 152 of the cylindrical cavity 151 of the upper casing, permitting the perfume to evaporate and dissipate over the air.

By means of the fixing seat 252 of the lower casing 20, the perfume bottle 1 can be stand stably on any place. Moreover, the double-face gum 253 of the bottoms of the legs of the fixing seat 252 enable the perfume bottle 1 to be fixed at a specific position.

It should be noted that the decorative articles 13, 23 can be replaceably fixed on the surfaces of the upper and lower casings 10, 20 by means of double-face gum or screws in a convenient manner.

The above embodiment is only used to illustrate the present invention, not intended to limit the scope thereof. Many modifications of the above embodiment can be made without departing from the spirit of the present invention.

What is claimed is:

1. Perfume bottle structure comprising:

an upper casing a top end of which is formed with a perforation, a surface of the upper casing being formed with several grooves at equal intervals, a decorative article being replaceably disposed on a surface defined between each two adjacent grooves, an edge of inner wall face of the upper casing being formed with locating plates, the upper casing being housed in a frame body a top end of the frame body being formed with a cylindrical cavity, a periphery of the cavity being formed with several slits and a central through hole, a locating post being disposed on one side of the through hole, a cylindrical sleeve having same structure being received in the cavity, the sleeve being formed with a central through hole and an arch slide slot beside the central through hole corresponding to the locating post, a decorative cap being fitted in the central through hole of the cylindrical cavity, a lug being disposed on the edge of the opening of the frame body;

a lower casing mated with the upper casing, a bottom end of the lower casing being formed with a perforation, a surface of the lower casing being formed with several grooves at equal intervals, a decorative article being replaceably disposed on a surface defined between each two adjacent grooves, a perfume container being placed into the internal chamber of the lower casing, an inner wall face of the lower casing being formed with several dents, an edge of the inner wall face of the lower casing being formed with recesses, the lower casing being housed in a frame body, a bottom end of the frame body being formed with a through hole, a fixing seat being disposed around the outer face of the through hole, each leg of the fixing seat being disposed with double-face gum, a connecting arm being disposed on the edge of the opening of the frame body corresponding to the lug; and a perfume container one end of which is formed with a narrowed neck section having an opening sealed by a cover body, a wick being positioned in the perfume container for absorbing the perfume and releasing the perfume into the air, a periphery of the bottom face of the perfume container being formed with notches at equal intervals and is equipped with a base seat, an inner wall face of the base seat being formed with ribs at equal intervals corresponding to the notches, the bottom of the base seat being disposed with several locating projections.

* * * * *